Figure 1:
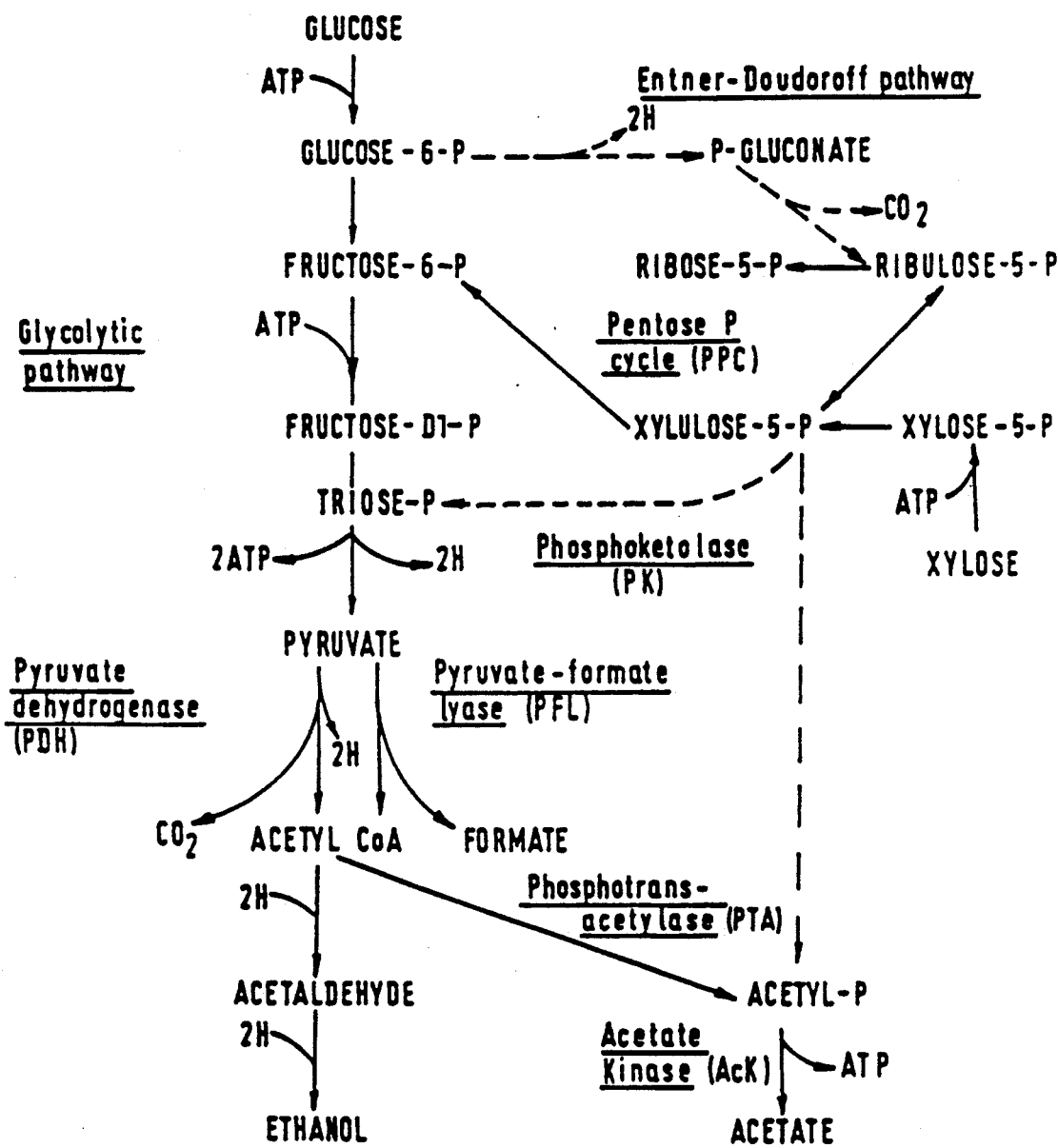

United States Patent [19]
Hartley

[11] Patent Number: 5,182,199
[45] Date of Patent: Jan. 26, 1993

[54] THERMOPHILIC ETHANOL PRODUCTION IN A TWO-STAGE CLOSED SYSTEM

[76] Inventor: Brian S. Hartley, Grove Cottage, Smith Street, Elsworth, Cambridge, England, CB3 8HY

[21] Appl. No.: 742,515

[22] PCT Filed: May 24, 1988

[86] PCT No.: PCT/GB88/00411
§ 371 Date: Nov. 27, 1989
§ 102(e) Date: Nov. 27, 1989

[87] PCT Pub. No.: WO88/09379
PCT Pub. Date: Dec. 1, 1988

Related U.S. Application Data

[63] Continuation of Ser. No. 435,480, Nov. 27, 1989, abandoned.

[30] Foreign Application Priority Data

May 27, 1987 [GB] United Kingdom ................ 8712410

[51] Int. Cl.⁵ .......................... C12P 7/14; C12P 7/06; C12P 7/08
[52] U.S. Cl. .................................. 435/162; 435/161; 435/163; 435/165; 435/252.5; 435/813
[58] Field of Search ............... 435/161, 163, 162, 165, 435/801, 813, 252.5, 252.31, 832

[56] References Cited

U.S. PATENT DOCUMENTS 4,329,433 5/1982 Seebeck et al. ..................... 435/813

OTHER PUBLICATIONS

Heinritz, B. Et al., "Yield Coefficients in Dependence on Milieu Conditions and Cell States", J. Basic Microbiol. 25(10) pp. 26–28, 1985.
R. Soc. Lond. A 321, pp. 555–568, 1987.
Wiegel, J., "Formation of Ethanol by Bacteria A Pledge for the use of Extreme Thermophilic Anaerobic Bacteria in Industrial Ethanol-Fermentation Processes", Experentia 36 pp. 1434–1446 1980.
Hartley et al., "Industrial Prospects for Thermophiles and Thermophilic Enzymes," Biochem. Soc. Symp. 48, pp. 133–146 1983.
B. S. Hartley, M. A. Payton & D. L. Pyle (1983) "Development and Economics of a Novel Thermophilic Ethanol Fermentation" In; Biotech 83, On-Line Publications Ltd. Norhtwood, UK. pp. 895–905.
Philosophical Transactions of the Royal Society of London, A. Mathematical and Physical Sciences, vol. 321, No. 1561, Apr. 30, 1987, The Royal Society (London GB), B. S. Hartley & G. Shama (1987) "Novel Ethanol Fermentations From Sugar Cane and Straw" pp. 555–568, see pp. 559–567.
M. A. Payton (1984) "Production of Ethanol by Thermophilic Bacteria". Trends in Biotechnology, 2, 153–158.
M. A. Payton & B. S. Hartley (1983) "Mutants of Bacillus stearothermophilus lacking NAD—linked L-lactate dehydrogenase" FMS Microbiol. Lett. 26, 333–336.
B. S. Hartley and M. A. Payton (1983) "Industrial Prospects for Thermophiles and Thermophilic Enzymes" Biochem. Soc. Symp. 48, 133–146.

(List continue on next page.)

Primary Examiner—Douglas W. Robinson
Assistant Examiner—Marian C. Knode
Attorney, Agent, or Firm—Larson and Taylor

[57] ABSTRACT

Production of ethanol by a process in which a strain of Bacillus stearothermophilus or other thermophilic, facultatively anaerobic bacterium is selected for the characteristics of fermenting sugars both aerobically and anaerobically and of being active in anaerobic fermentation at 70° C. or above and (i) anaerobic fermentation is carried out with continuing removal of ethanol at 70° C. or above; (ii) the fermentative activity of the bacterium is maintained by withdrawing a proportion of the anaerobic fermentation medium on a continuing basis preferably with removal of ethanol and allowing the bacteria therein to multiply aerobically, using residual sugars or metabolites thereof present in the medium, before being returned to the anaerobic fermentation.

9 Claims, 6 Drawing Sheets

OTHER PUBLICATIONS

M. A. Payton (1984) "Production of Ethanol by Thermophilic Bacteria". Trends in Biotechnology, 2, 153–158, This review recapitulates much of our earlier work.

B. S. Hartley & G. Shama (1987) "Novel Ethanol Fermentations From Sugar Cane and Straw" Phil Trans Roy Soc Lond A321 555–568.

B. S. Hartley, D. J. Leak, S. Amartey, P. Goddard, G. da Silva and R. San Martin (1987) "Fermentation Ethanol From Straw" In: Straw, A Valuable Raw Material. vol. 1. Paper Industries Research Association, Leatherhead, Surrey, UK.

A. Atkinson, D. C. Ellwood, C. G. T. Evans and R. G. Yeo, Production of alcohol by *Bacillus stearothermophilus, Biotech. Bioeng.,* 17, 1375–1377, (1975a).

T. D. Brock, *Thermophilic microorganisms and life at high temperatures*, Ed. M. P. Starr, Springer-Verlag, New York (1978). (Introduction only).

L H. Carreira, J. Wiegel and L. G. Ljungdahl, Production of ethanol from biopolymers by anaerobic, thermophilic, and extreme thermophilic bacteria: I. Regulation of carbohydrate utilizaton in mutants of *Thermoanaerobacter Ethanolicus, Biotechnol. Bioeng. Symp.,* No. 13, 183–191, (1983).

L. H. Carreira and L. G. Ljungdahl, Production of ethanol from biomass using anaerobic thermophilic bacteria, in Liquid Fuels Developments, Ed. D. L. Wise, CRC Press, Boca Raton, Fla., USA, (1983), (Chapter 1 only).

V. Kannan and R. Mutharasan, Ethanol fermentation characteristics of *Thermoanaerobacter ethanolicus, Enzyme Microb. Technol.,* 7, 87–89, (1985).

L. S. Lacis and H. G. Lawford, Effect of growth rate on ethanol production by *T. ethanolicus* in glucose or xylose limited continuous culture, *Biotechnol. Letters,* 10, 603–608, (1988).

R. Lamed and J. G. Zeikus, Glucose fermentation pathway of *Thermoanaerobium brockii J. Bacteriol.,* 141, 1251–1257, (1980).

L. G. Ljungdahl, F. Bryant, L. Carreira, T. Saiki and J. Wiegel, Some aspects of thermophilic and extreme thermophilic anaerobic microorganisms, In: *Trends in the biology of fermentations for fuels and chemicals*, Ed. A Hollaender, Basic Life Sciences, 18, 397–419, Plenum Press, New York, (1981).

R. San Martin, S. Amartey, D. Bushell, D. J. Leak and B. S. Hartley, Continuous ethanol fermenation with cell recycle using a thermophilic facultative anaerobe, *Energy from Biomass Series 4*, Eds. G. Grassi, D. Pirrwitz and H. Zibetta, pp. 383–393, Elsevier, London, (1989).

K. Skoog and B. Hahn-Hagerdal, Xylose fermenation, *Enzyme Microb. Technol.,* 10, 66–80 (1988).

B. Sonnleitner, Biotechnology of thermophilic bacteria-growth, products and application, *Adv. Biochem. Eng. Biotechnol.,* 28, 69–135, (1983).

B. Sonnleitner and A. Fietcher, Advantages of using thermophiles in biotechnological processes: expectations and reality. *Trends in Biotechnol.,* 1, 74–80, (1983).

J. Wiegel and L. G. Ljungdahl, The importance of thermophilic bacteria in biotechnology, *Crit. Rev. Biotech.,* 3, 39–108, (1986).

J. Wiegel and L. G. Ljungdahl, *Thermoanaerobacter ethanolicus* gen. nov. spec. nov., a new extreme thermophilic, anaerobic bacterium, *Arch. Microbiol.,* 128, 343–348, (1981).

J. Wiegel, L. H. Carriera, Ch. P. Mothershed, and J. Puls, Production of ethanol from biopolymers by anaerobic, thermophilic and extreme thermophilic bacteria, II. *Thermoanaerobacter ethanolicus* JW 200 and its mutants in batch cultures and resting cell experiments, *Biotechnols. Bioeng. Symp.,* No. 13, 193, (1983).

J. G. Zeikus, P. W. Hegge, and M. A. Anderson, *Thermoanaerobium brockii* gen. nov. and sp. nov., A new chemoorganotrophic, caldoactive, anaerobic bacterium, *Arch. Microbiol,* 122, 41–48, (1979a).

J. G. Zeikus, Thermophilic bacteria: ecology, physiology and technology, *Enzyme Microb. Technol.,* 1, 243–252, (1979b).

J. G. Zeikus, A. Ben-Bassat, T. K. Ng, and R. J. Lamed, Thermophilic ethanol fermentations, In: *Trends in the Biology of Fermentations for Fuels and Chemicals,* Ed. A. Hollaender, Plenum Press, New York, 441, (1981).

J. Bacteriol (1976) vol. 126(1), pp. 520–533.

Biotechnol and Bioeng (1975) vol. 17(9) pp. 1375–1377.

THERMOPHILIC ETHANOL PRODUCTION IN A TWO-STAGE CLOSED SYSTEM

This application is a continuation of application Ser. No. 435,480, filed Nov. 27, 1989, now abandoned.

FIELD OF INVENTION

The invention relates to alcohol, that is to say ethanol, production by fermentation.

GENERAL DISCUSSION

Alcohol production from waste or by-product sugars whether arising as such or derived from conversion of other carbohydrates has long been known but is currently of growing importance. Cheap oil at present, and severe food shortages in particular regions, cannot detract from the basic unsoundness of relying on non-renewable energy sources when, properly managed, agriculture could provide food and energy world wide.

We have studied known alcohol production processes, largely by yeasts, and concluded that a key improvement in economic operation, if achievable in practice, is use of temperatures at which the alcohol can conveniently be removed directly as vapour from the fermentation medium. Yeasts of course are incapable of growth at such temperatures, and we have turned to thermophilic bacteria.

Yeasts ferment only glucose, maltose or sucrose whereas some bacteria can also utilise cellobiose from enzymic hydrolysis of cellulose or xylose and arabinose from hydrolysis of hemicellulose. The latter (pentose) sugars are the major components of waste streams from paper-making or from pretreatments of straw such as steam-explosion or dilute acid hydrolysis. The economics of ethanol production from sugar cane would for example be greatly improved if the bagasse could be so utilised as well as the juice.

Some thermophiles have been described which can utilise all these sugars to produce high yields of ethanol e.g. *Clostridium thermosaccharolyticum*, *Cl. thermohydrosulfuricum* or *Thermoanaerobacter ethanolicus*. However they are strict anaerobes and their reported properties compare unfavourably with the *Bacillus stearothermophilus* strains described below. Moreover we have seen that facultative anaerobes have additional advantages by allowing a novel mixed aerobic-anaerobic process which allows by-products of the anaerobic phase to be utilised aerobically to regenerate catalytic biomass.

Most facultative anaerobes do not produce high yields of ethanol. In previous disclosures we described a 'metabolic steering' strategy whereby mutants believed to be of *Bacillus stearothermophilus* NCA 1503 may be manipulated to make high yields of ethanol [1,2]. That strategy involved eliminating L-lactate production by selecting mutations in L-lactate dehydrogenase. The resulting mutant was expected to make acetate, ethanol and formate anaerobically in yields of 2:2:4 per mole of sucrose. Surprisingly however yields of ethanol were higher than this theoretical maximum under certain conditions, notably low pH and higher temperatures, and this was ascribed to a catalytic conversion of sucrose to ethanol + $CO_2$ during a final non-growth stage in batch cultures.

We have now discovered that the results previously reported are to an extent in error in that the organism described is not a derivative of *B. stearothermophilus* NCA 1503 (NCIB 8924) as we assumed (Payton and Hartley 3) nor indeed of any specific known thermophilic bacillus. Instead it appears to be derived from a novel strain of the species *Bacillus stearothermophilus* that has properties that make it much superior to known strains for the purposes described above. In particular, it has a much higher growth rate than strain NCA 1503 both aerobically and anaerobically at temperatures above 60° C. and grows anaerobically above 70° C., at which temperature growth ceases with strain NCA 1503. Moreover, it utilises both cellobiose and the pentose sugars found in a crude dilute acid hydrolysis of wheat straw produced by the ICI process described by Ragg and Fields [4].

Hence though this invention is not restricted to particular bacteria, it concerns facultative anaerobes such as *B. stearothermophilus* strain LLD-R (NCIB deposit details below) that rapidly ferment a wide range of sugars including cellobiose and pentoses both aerobically and anaerobically above 70° C. Such strains would normally produce lactate anaerobically, but this pathway is eliminated by selecting mutations in NAD-linked lactate dehydrogenase. Moreover acetate production may be suppressed by physiological controls such as acid pH, higher temperatures or high levels of extracellular acetate, or by further genetic lesions in enzymes of the acetate pathway. This leads to a channelling of anaerobic metabolism via pyruvate dehydrogenase, resulting in conversion of sugars to ethanol + $CO_2$. The resulting cells may not grow anaerobically but can catalyse conversion of sugars to ethanol without growth.

Hence an aspect of this invention is a process in which such cells are used in a catalytic anaerobic production stage fed with sugars but minimizing growth. Most of the ethanol is automatically removed into the vapour phase above 70° C., so the production phase can be fed with high sugar concentrations without exceeding the ethanol tolerance of the organism (ca. 4% w/v). We have seen that these properties lend themselves to a novel continuous process in which the optimum fermenter productivity is achieved by continuous cell recycle after removing aqueous phase products by centrifugation or filtration. The minimum growth rate necessary to maintain catalytic viability can be achieved by bleeding off a small proportion of cells during recycle; this results in conversion of an equivalent proportion of the influent sugar into fresh biomass. Alternatively, the remaining aqueous phase ethanol is removed before returning spent cells, unhydrolysed sugars, residual traces of ethanol and by-products such as acetate and formate to an aerobic 'biomass' stage. The aerobic cells are then returned to the catalytic 'production' stage, if necessary through an intervening anaerobic 'adaptation' stage. An attractive feature of such a reactor conformation is that automatic process control to optimise ethanol yield can be maintained by minimizing aerobic $CO_2$ and maximizing anaerobic $CO_2$.

HISTORY AND CHARACTERISTICS OF STRAINS

*Bacillus stearothermophilus* strain LLD-15 (NCIB deposit details below) arose during attempts to obtain mutants of *Bacillus stearothermophilus* strain NCA 1503 lacking L-lactate dehydrogenase activity by selecting for suicide substrate resistance (Payton and Hartley [3]). It was naturally assumed to be a mutant of the latter strain, but in fact it is derived from a novel extreme thermophile, *Bacillus stearothermophilus* strain LLD-R. Strain LLD-R arises spontaneously and reproducibly from reversion of strain LLD-15 and is selected on plates or during continuous cultures under which it grows more rapidly, e.g. at low pH in media containing sugars+acetate and formate. It produces L-lactate anaerobically and contains high levels of L-lactate dehydrogenase so it is clearly a 'wild-type' revertant of the LLD-15 lesion.

Both the mutant *B. stearothermophilus* strain LLD15 and the wild-type, strain LLD-R, are gram positive, spore-forming rods that resemble the broad class *Bacillus stearothermophilus* in morphology and growth temperature range. However in a series of biochemical and growth tests (Table 1) they differ from *B. stearothermophilus* NCA 1503 and all other related strains in the extensive collection of Sharp et. al. *J. Gen. Microbial* 117 201 (1980). These properties merit a general classification as *Bacillus stearothermophilus* following Donk, L. (1920) *J. Bacteriol.* 5 373, but the growth temperature range is distinctly higher than that for strain NCA 1503, from which the mutant was thought to derive. Hence both organisms are deposited as novel type strains *Bacillus stearothermophilus* LLD-R (NCIB 12403) and *Bacillus stearothermophilus* LLD-15 (NCIB 12428) with the National Collection of Industrial and Marine Bacteria, Torry Research Station, P.O. Box 31, Aberdeen, AB9 8DG, Scotland. The respective dates of deposit are Feb. 10, 1987 and Apr. 9, 1987.

Strains LLD-R and LLD-15 grow well on a rich BST medium (g/1): tryptone (Oxoid) 20.0; yeast extract (Oxoid) 10.0; $K_2SO_4$, 1.3; $MgSO_4.7H_2O$, 0.27; $MnCl_2 4H_2O$, 0.015; $FeCl_3.6H_2O$, 0.007; citric acid, 0.32; supplemented with an appropriate carbon source and adjusted to the required pH with KOH or $H_2SO_4$. However we have also developed a fully defined Medium BST-MM (g/1): C source variable; $K_2SO_4$, 0.3; $Na_2HPO_4$, 1.0; $MgSO_4$, 0.4; $MnCl_2.4H_2O$, 0.003; $CaCl_2$, 0.005; $NH_4Cl$, 1.0; citric acid, 0.16; methionine, 0.2; (mg/1): nicotinic acid, 10; biotin, 10; thiamine, 10; $ZnSO_4.7H_2O$, 0.4; boric acid, 0.01; $CoCl_2.6H_2O$, 0.05; $CuSO_4.5H_2O$, 0.2; $NiCl_3.6H_2O$, 0.01; EDTA, 0.25.

TABLE 1

Comparison of new strains with other thermophilic bacilli

| | B. stearo. LLD-15 | B. stearo. LLD-R | B. stearo. NCA 1503 | B. stearo. ATCC 12016 |
|---|---|---|---|---|
| Starch hydrolysis | R | .. | + | + |
| Casein hydrolysis | + | .. | + | w |
| Gelatin hydrolysis | + | .. | + | w |
| Hippurate hydrolysis | + | .. | — | .. |
| Citrate utilisation | — | — | — | .. |
| Catalase | + | + | — | — |
| Oxidase | — | — | — | + |
| Growth in 3% saline | — | .. | w | — |
| Sugar fermentations: | | | | |
| Galactose | — | — | w | + |
| Glycogen | — | .. | + | w |
| Mannitol | — | — | — | w |
| Raffinose | — | — | + | — |
| Starch | — | .. | + | — |
| Trehalose | + | .. | + | — |
| Xylose | + | + | — | + |

| | B. stearo. 240 | B. stearo. 262 | B. stearo. RS93 | B. stearo. 126 |
|---|---|---|---|---|
| Starch hydrolysis | R | R | — | — |
| Casein hydrolysis | + | + | — | — |
| Gelatin hydrolysis | — | + | — | w |
| Hippurate hydrolysis | .. | .. | .. | .. |
| Citrate utilisation | .. | .. | .. | .. |
| Catalase | + | + | + | + |
| Oxidase | + | + | + | + |
| Growth in 3% saline | w | + | + | w |

TABLE 1-continued

Comparison of new strains with other thermophilic bacilli

| Sugar fermentations: | | | | |
|---|---|---|---|---|
| Galactose | — | — | — | — |
| Glycogen | + | + | — | — |
| Mannitol | — | — | + | + |
| Raffinose | — | — | — | — |
| Starch | + | w | — | — |
| Trehalose | + | — | w | w |
| Xylose | — | — | — | — |

| | B. stearo. 10 | B. caldotenax | B. caldovelox |
|---|---|---|---|
| Starch hydrolysis | + | R | R |
| Casein hydrolysis | + | + | + |
| Gelatin hydrolysis | + | + | + |
| Hippurate hydrolysis | .. | + | .. |
| Citrate utilisation | .. | + | .. |
| Catalase | — | — | — |
| Oxidase | — | + | + |
| Growth in 3% saline | w | w | — |
| Sugar fermentations: | | | |
| Galactose | w | — | — |
| Glycogen | + | w | — |
| Mannitol | — | w | + |
| Raffinose | + | + | w |
| Starch | + | — | — |
| Trehalose | + | w | + |
| Xylose | + | — | — |

| | B. caldolyticus | B. coagulans ATCC 8083 | B. coagulans ATCC 12245 |
|---|---|---|---|
| Starch hydrolysis | + | — | — |
| Casein hydrolysis | + | — | w |
| Gelatin hydrolysis | + | — | — |
| Hippurate hydrolysis | .. | .. | .. |
| Citrate utilisation | .. | .. | .. |
| Catalase | ± | + | + |
| Oxidase | + | — | — |
| Growth in 3% saline | — | — | — |
| Sugar fermentations: | | | |
| Galactose | — | + | + |
| Glycogen | + | w | — |
| Mannitol | w | w | — |
| Raffinose | — | — | — |
| Starch | + | w | w |
| Trehalose | + | + | + |
| Xylose | — | w | w |

Test were performed in parallel according to Sharp, R. J., Bown, K. J. and Atkinson R. (1980) on *B. stearothermophilus* strain LLD-15, LLD-R and NCA 1503 and *B. caldotenax*. The other data are from that reference; R, restricted; +, positive; w, weak positive; —, negative; .., not tested.

LIST OF FIGURES

The text refers to FIGS. 1-6 which are as follows:

FIG. 1—Anaerobic pathways and theoretical yields in *Bacillus stearothermophilus* strain LLD-15

FIG. 2—Steady state values in continuous cultures at pH7, $D=0.2$ hr$^{-1}$ on sucrose 10 g/1 anaerobically or 5 g/1 aerobically (dotted line), 0.5% tryptone, 0.25% yeast extract (a) Biomass: (●) strain NCA 1503, (■)strain LLD-R, (○) strain LLD-15

(b) Products with strain LLD-15

Figure 3:
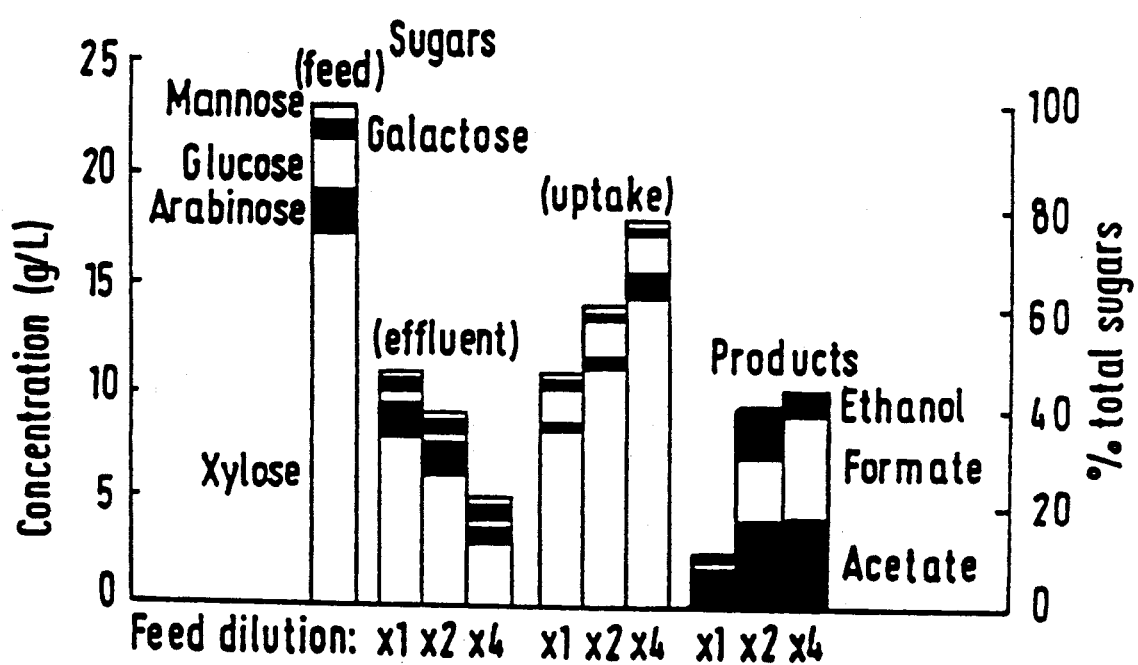

FIG. 3—Continuous cultures of strain LLD-15 on various concentrations of wheat-straw hydrolysate (Ragg and Fields, 1986) at 70° C., $D=0.2hr^{-1}$, pH7.

Figure 4:
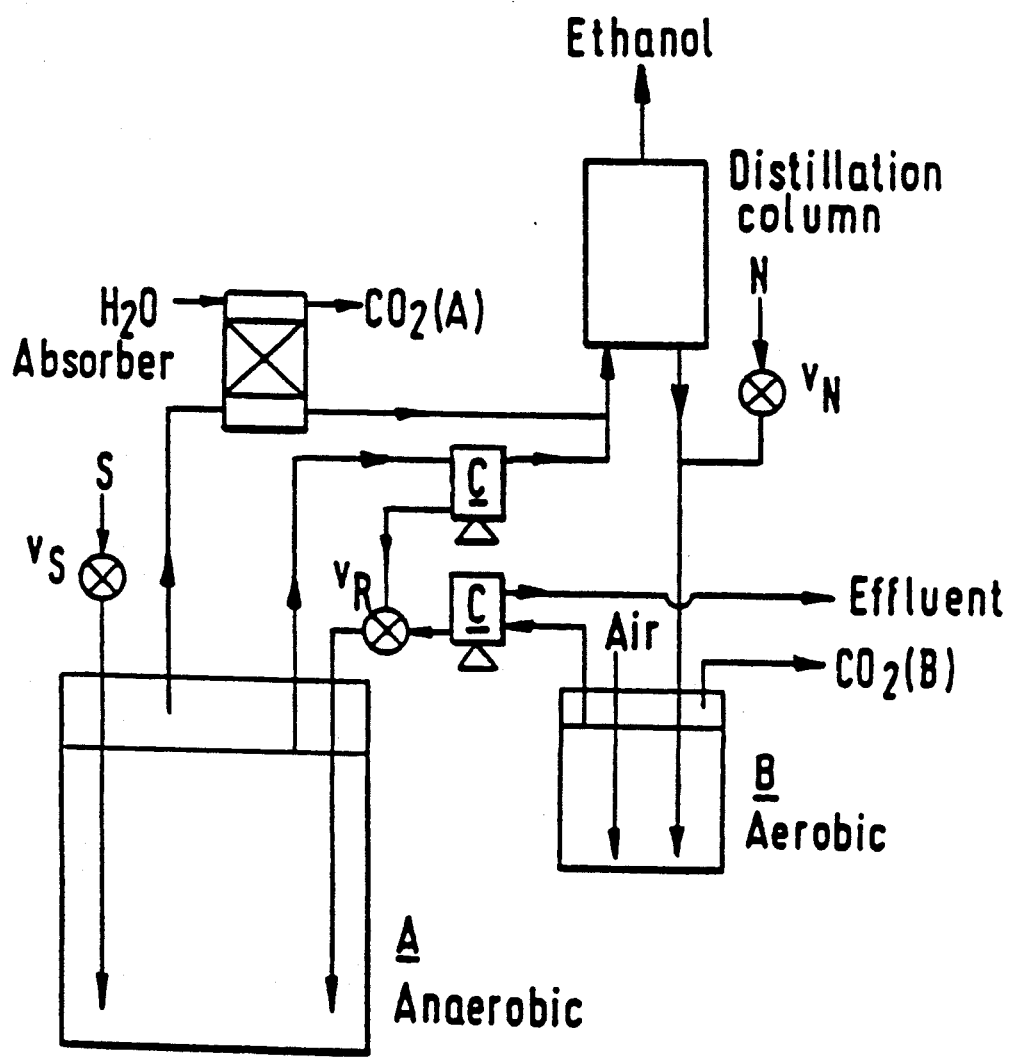

FIG. 4—A continuous two-stage reactor system for ethanol production.

Figure 5:
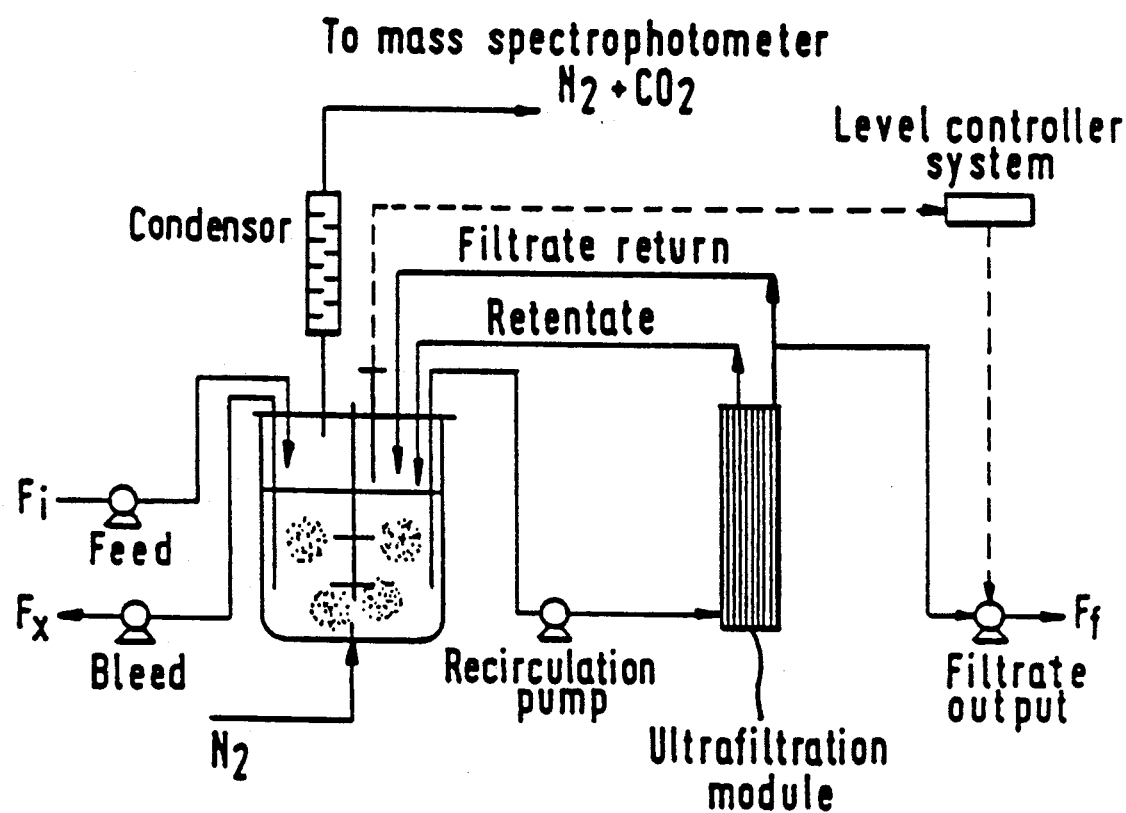

FIG. 5—Continuous fermentation with partial cell recycle, plant.

Figure 6:
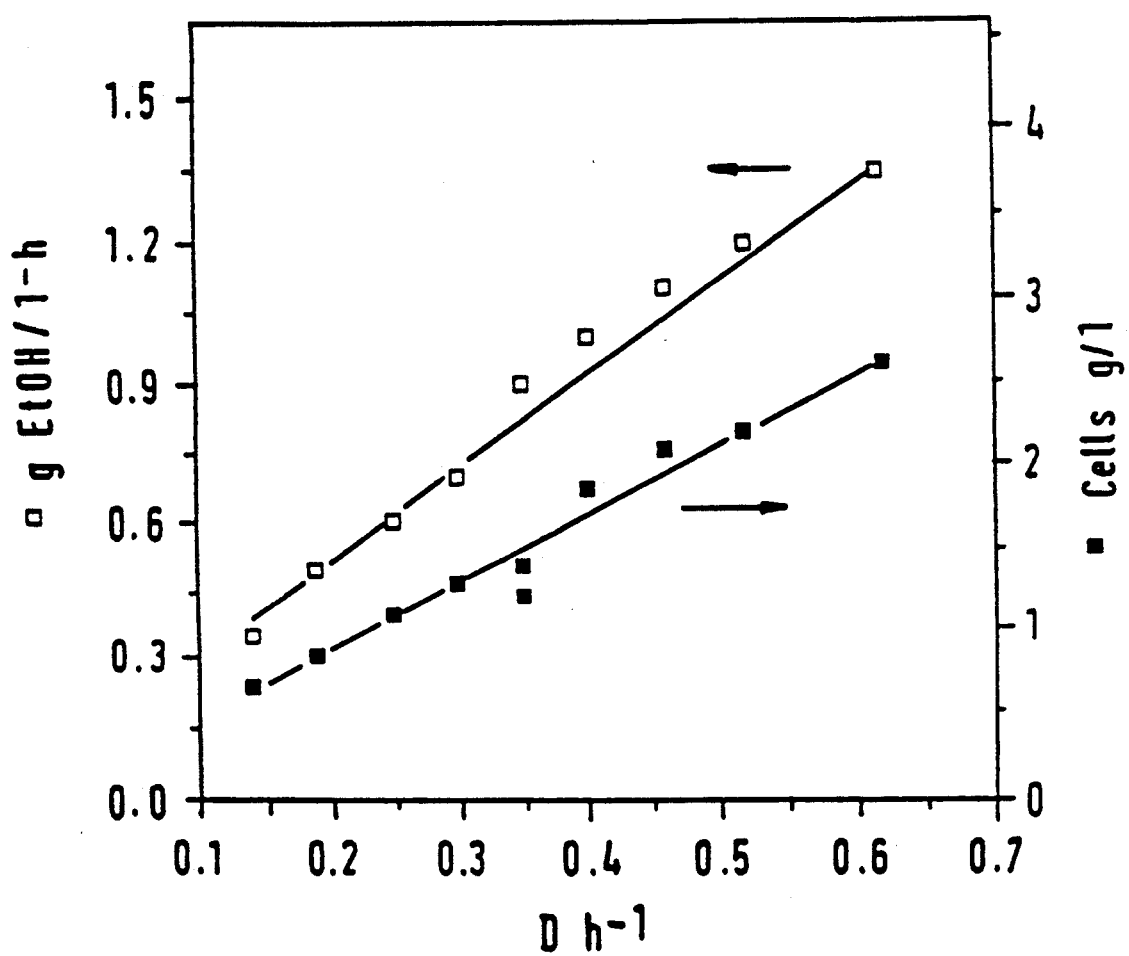

FIG. 6—Continuous fermentation with partial cell recycle, relationships.

ANAEROBIC PATHWAYS IN THE NEW STRAINS

Our original experiments were conducted mostly at 60° C. in batch culture on 2.35% w/v) sucrose/BST medium since that is the optimal temperature for strain NCA 1503 which was the presumed ancestor of the mutant strain LLD-15. In anaerobic batch cultures of strain NCA 1503 or strain LLD-R the final product is predominantly L-lactate, whereas strain LLD-15 gives (moles/mole sucrose): ethanol (1.8), acetate (1.8) and formate (3.2) at pH 7.9. This is consistent with metabolism via the pyruvate-formate lyase (PFL) pathway (FIG. 1) since the mutation abolishes L-lactate dehydrogenase activity. However at more acid pH the ratio of ethanol to acetate increases becoming at pH 6.2: ethanol (2.9), acetate (0.2) and formate (1.3). This indicates that a novel pathway leading to 2 ethanol+2 $CO_2$ from each glucose residue is also operating, and we believe that this is via pyruvate dehydrogenase (PDH) which is generally considered to be inoperative anaerobically. In summary the products in FIG. 1 are:

| Pathway | Products (moles/mole sugar) | | | | |
|---|---|---|---|---|---|
| | Ethanol | Acetate | Formate | $CO_2$ | ATP |
| Glucose: | | | | | |
| Glycolysis + PDH | 2.00 | 0.00 | 0.00 | 2.00 | 2.00 |
| Glycolysis + PFL | 1.00 | 1.00 | 2.00 | 0.00 | 3.00 |
| Entner-Doudoroff + PDH | 1.50 | 0.50 | 0.00 | 0.00 | 3.00 |
| Entner-Doudoroff + PFL | 1.00 | 1.00 | 1.00 | 1.00 | 2.00 |
| Xylose: | | | | | |
| Pentose cycle + PDH | 1.67 | 0.00 | 0.00 | 1.67 | 1.67 |
| Pentose cycle + PFL | 0.83 | 0.83 | 1.67 | 0.00 | 2.50 |
| Phosphoketolase + PDH | 1.00 | 1.00 | 0.00 | 1.00 | 1.50 |
| Phosphoketolase + PFL | 0.50 | 1.50 | 1.00 | 0.00 | 2.50 |

The switch from the PFL- to the PDH-pathway occurs in the later stages of anaerobic batch fermentations with strain LLD-15 and is associated with a slowing in growth rate and the appearance of traces of pyruvate in the medium. The effect is most marked during batch fermentations on high sugars, e.g. 5% (w/v) sucrose, where growth ceases long before all the sugar is utilised but the non-growing cells continue to convert sucrose quantitatively to ethanol+$CO_2$. Hence in such a batch fermentation ethanol yields can reach 3.64 moles/mole sucrose (91% theoretical). Higher temperature (70° C.) also favours a switch to the PDH-pathway.

The switch from the PFL to the PDH pathway is due to accumulation of acetate and formate in the medium, and not due to ethanol accumulation, as shown by adding these products to the medium in the early stages of a batch fermentation. Pyruvate secretion is observed whenever the PDH-pathway is significantly operative. Cells grown under such conditions show levels of pyruvate dehydrogenase activity in cell-free extracts even higher than those in fully aerobic cells, whereas the wild-type shows very low anaerobic PDH levels. There is no detectable pyruvate decarboxylase or formate dehydrogenase activity, which might have provided an alternative pathway for ethanol and $CO_2$ production. The switch in pathways may be a pre-sporulation phenomenon as biomass decreases towards the end of batch fermentations and spores are observed.

The probable reason for the switch in pathways is as follows. The wild type organism is geared to rapid growth, both aerobic and anaerobic, so has rapidly acting sugar uptake and glycolysis systems. It normally secretes L-lactate under anaerobic conditions, but when that pathway is blocked pyruvate metabolism is shunted into the PFL-pathway. However the rate of excretion of acetate and formate then becomes the rate-limiting step for energy metabolism, particularly in the presence of external acetate and formate or at acid pH where secretion against an anion or proton gradient reduces the efflux rate. Hence pyruvate accumulates within the cell and induces the pyruvate dehydrogenase activity to levels even higher than in fully aerobic cells. The flux through pyruvate dehydrogenase is however still inadequate to maintain the rapid growth rate seen at alkaline pH or at low sugar concentration in the absence of acetate and formate, and the cells reach a stationary stage in which sugars are converted quantitatively to ethanol and $CO_2$ without growth.

SINGLE STATE CONTINUOUS CULTURES

Preliminary experiments to compare wild type (strain LLD-R) and strain LLD-15 were conducted with 2-3% sucrose in BST medium at 60° C. (dilution rate 0.25 $hr^{-1}$). As expected, wild type cells produced predominantly L-lactate, ranging from 3.13 moles/mole sucrose consumed at pH8 to 3.50 at pH 6.35 and Y values (g.cells/g.sucrose) were around 0.07. With the mutant strain at pH7 ethanol was the major product (2.3 moles/mole sucrose) and the Y value was higher (0.10). However strain LLD-15 was unstable in continuous cultures at acid pH or at high sugar concentrations, and takeover by revertants to L-lactate production (strain LLD-R) was common. This reflects the powerful selection pressure for increased energy efficiency exerted by such continuous cultures, and illustrates a potential defect of a continuous process. However this reversion is less frequent in continuous cultures at 70° C. on lower sugar concentrations and can be eliminated by reselection from strain LLD-R of a non-reverting mutant (procedure of Payton and Hartley[3]).

Figure 2A:
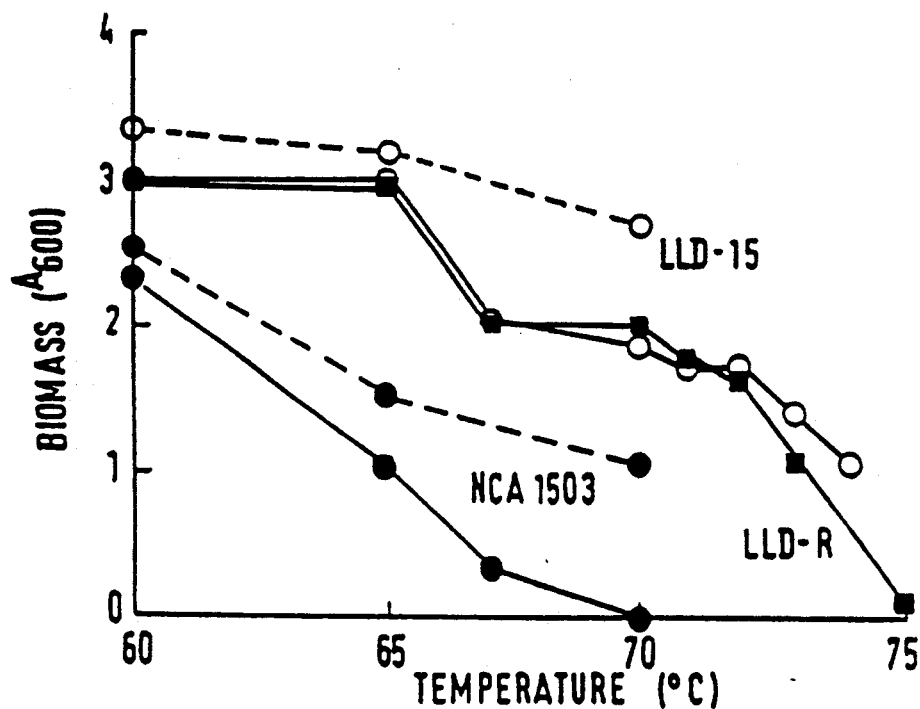

FIG. 2a shows the steady-state biomass in continuous cultures of strains NCA 1503, LLD-R and LLD-15 grown anaerobically on 1% (w/v) sucrose or aerobically on 0.5% sucrose, 0.5% tryptone, 0.25% yeast extract at pH7.0, dilution rate 0.2 $hr^{-1}$, at various temperatures. Both the new strains and strain NCA 1503 show efficient aerobic and anaerobic metabolism, but strain NCA 1503 expires anaerobically above 70° C. whereas both the wild-type (LLD-R) and the mutant (LLD-15) retain significant anaerobic metabolism up to 75° C. This temperature is closer to the boiling point of aqueous ethanol and is therefore significant for the processes described herein.

Figure 2B:
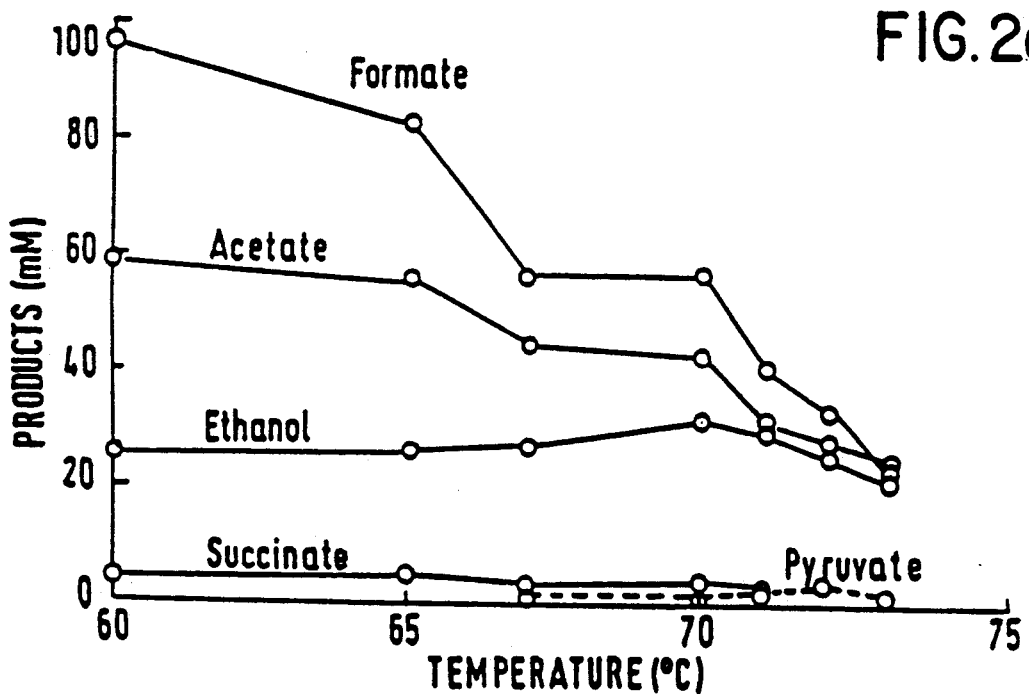

The products from the anaerobic continuous cultures of strain LLD-15 are shown in FIG. 2b. It is clear that ethanol productivity (mmol/$A_{600}$) rises as temperature increases and is associated with pyruvate secretion.

Strain NCA 1503 does not grow on xylose either aerobically or anaerobically, but both LLD-R and LLD-15 do. The results with sucrose can be compared with continuous cultures on 1% xylose at 70° C. in analogous conditions (Table 2). Steady states can again be maintained and alcohol yields are again higher at acid pH.

TABLE 2

Continuous anaerobic cultures of strain LLD-15 on xylose (10 g/l), tryptone (5 g/l), yeast extract (2.5 g/l), BST salts at 70° C., D = 0.2 hr$^{-1}$

| pH | Cells (g/l) | Residual Xylose (g.l) | Products: (moles/mole xylose, g/g cells/hr) | | |
|---|---|---|---|---|---|
| | | | Ethanol | Acetate | Formate |
| 6.5 | 0.35 | 0.9 | 1.70 (0.13) | 1.79 (0.17) | 3.48 (0.25) |
| 7.0 | 0.98 | 0.9 | 1.43 (0.04) | 2.14 (0.07) | 3.84 (0.10) |
| 8.0 | 0.67 | 0.9 | 0.82 (0.03) | 1.07 (0.05) | 2.20 (0.08) |

The steady state biomass at pH7 is less than that with the concentration of sucrose so xylose metabolism is less energy efficient. Sucrose is believed to be metabolised to two hexose phosphates via a relevant kinase+phosphorylase, requiring one ATP. In contrast two ATP's are believed necessary to product two pentose phosphate molecules. Hence sucrose is intrinsically a better energy substrate.

The products of the continuous xylose fermentations show that an appreciable proportion of the tryptone-yeast extract is metabolised for energy production. Nevertheless the product ratios at pH8 indicate that metabolism proceeds via the pentose phosphate pathway, glycolysis and the PFL-pathway. The ethanol yields are lower than on sucrose, suggesting little flux through the PDH-pathway. However fermentations on higher sugar concentrations at higher temperatures and lower pH are expected to increase the flux through the latter pathway, as for sucrose, and mutations in acetate kinase or phosphotransacetylase to produce a non-growing strain that converts xylose quantitatively to ethanol and $CO_2$.

Hence the new strain and derivatives thereof are an organism of choice for ethanol production from hydrolysates of lignocellulosic wastes. Continuous cultures have been performed on crude hydrolysates of wheat straw produced by the ICI hydrolysis process described by Ragg and Fields[4]. This is effectively a waste stream, rich in xylose and lignin, produced by a short dilute acid hydrolysis step designed to remove hemicelluloses and thereby facilitate subsequent delignification. The crude material is adjusted to pH7.0 and tested in continuous culture with the new strain at 70° C., D=0.2 hr$^{-1}$ at various dilutions as shown in FIG. 3. The waste-stream provides all necessary nutrients for continuous culture of the organism and all the sugars are utilised to some extent. Ethanol yields increase at lower pH and the product ratios are consistent with metabolism via the pentose phosphate pathway, glycolysis and PFL plus PDH (see FIG. 1).

A TWO-STAGE AEROBIC/ANAEROBIC FERMENTATION

The property of quantitative conversion of sugars to ethanol without growth is a significant potential advantage of the new strain. It can be maximised by further manipulation of physiological constraints, as illustrated above, or by selection of further mutations. FIG. 1 shows that cells lacking acetate kinase or acetyl CoA-phosphotransacetylase cannot produce acetate. Since acetate secretion is essential to maintain anaerobic flux through PFL, only the PDH-pathway remains open for pyruvate metabolism resulting in ethanol+$CO_2$. Such cells may not grow anaerobically but can be produced aerobically and used anaerobically to convert sugars to ethanol catalytically.

Moreover we have seen that mutations that increase intracellular pyruvate dehydrogenase activity will increase ethanol productivity, since PDH appears to limit energy flux. Such mutations will be selected, either spontaneously or after mutagenesis, by growth in continuous culture or on plates under conditions in which intracellular acetate and formate accumulation occur, i.e. on sugars at low pH+added acetate and formate. Alternatively additional copies of the PDH-genes can be introduced by genetic engineering protocols.

Since maximum ethanol productivity is associated with cessation of growth, conventional anaerobic batch cultures are unsuitable for ethanol production by such strains. Batch production may be achieved by introducing a large inoculum of cells grown aerobically into the anaerobic reactor, or by conducting batch fermentations under conditions of partial anaerobiosis, where the total biomass will depend on the level of oxygen supplied.

Moreover an indefinite continuous process catalysed by non-growing cells is clearly impossible; a minimum uptake of sugar (maintenance coefficient, $m_3$) is needed to maintain cell viability. We have seen that this can be achieved in a single-stage anaerobic reactor with partial cell recycle such as that illustrated in FIG. 5 without recycle or bleed; the system operates as a conventional single-stage continuous culture through the level controller system. When this is blocked and recycle begins, biomass levels rise to a maximum dictated by the maintenance coefficient. Thereafter *all* substrate is converted to products. This is clearly advantageous for production purposes, but will in practice lead to steadily decreasing (m) reactor productivity. However if a small bleed is taken from the reactor ($F_x$), steady-state growth occurs at a rate $\mu = F_x/V$ (where V=reactor volume). This can be minimised to balance declining reactor productivity. In the figure, sugars and nutrients are pumped in at a rate $F_i$. A constant bleed $F_x, (F_x << F_i)$ determines the cell growth rate $\mu/=F_x/V$, (V=fermentor volume). The remaining broth is recirculated through a hollow fiber ultrafiltration membrane, operated at its maximum capacity. The filtrate output $F_f$ is controlled by a level controller system; the excess filtrate is returned to the fermentor.

FIG. 6 shows the results of a model system with strain LLD-15 on 1% sucrose/BST AM at 70° C., pH 7. The figure shows the relation between volumetric ethanol productivity, cell concentration and total dilution rate, $D=F_i/V$. $S_o=1\%$, T 70° C., 400 rpm, pH 7.0 *Bacillus stearothermophilus* LLD-15. Cell growth rate $\mu=F_x/V=0.1$ h$^{-1}$. The growth rate was kept constant at 0.1 h$^{-1}$, by fixing the bleed rate $F_x$. The overall dilution rate D was increased by increasing the sugars and nutrients feed rate $F_i$. Sucrose consumption (not shown) was always above 97% indicating a high stability of the system. The volumetric ethanol productivities were significantly higher than conventional single stage continuous fermentations (i.e. 0.6 g ethanol/1-h). This was primarily due to the proportional increase in cell density achieved at high dilution rates.

Such reactor systems are feasible for ethanol production by these strains, but we have seen that the special properties of a facultative anaerobe can be maximised for ethanol production in the novel reactor configuration illustrated in FIG. 4. In summary, sugars are pumped into the anaerobic reactor A at rate $V_2$. Vapour phase ethanol is separated from $CO_2$ by water absorption. A portion of spent cells is removed by centrifugation (C) and ethanol distilled from the effluent stream. The residual sugars and ethanol are supplemented with nutrients (N) at rate $V_n$ and used to create catalytic biomass aerobically (B). The resulting cells are returned to reactor A after centrifugation. In more detail sugars such as cane-juice, molasses, straw-hydrolysate, etc., are fed at rate $V_S$ into an anaerobic reactor supplied by cells at rate $V_R$. For the purpose of illustration the reactor A is a simple stirred tank (volume $V_A$) in which temperature and pH are controlled to maximise ethanol yield and productivity. Ethanol in the vapour phase is separated from $CO_2$ by absorption with water before continuous distillation. However one of the major advantages of a thermophilic fermentation is that as the boiling point of aqueous ethanol is approached it can be removed continuously and economically from the aqueous phase to remove ethanol inhibition of growth and/or productivity (in the case of strain LLD-15, growth ceases above 4% (w/v) ethanol at 60° C.). This allows the use of higher concentrations of sugars as feedstock, such as molasses. Hence the anaerobic reactor may with advantage be one that maximises rate of ethanol removal into vapour phase such as vacuum fermentation, sparging with recycled $CO_2$ or continuous recycling through a vacuum flash evaporator.

Most of the cells in the effluent from A are concentrated by continuous centrifugation and recycled. Then ethanol is removed from the supernatant by continuous distillation. The stream entering the aerobic reactor B will contain spent cells (or spores), residual ethanol, unutilised sugars and by-products such as acetate and formate. Most of these can serve as aerobic substrates for strain LLD-15. Hence the stream is supplemented with necessary nutrients to allow maximum conversion of these waste carbon sources to biomass.

That biomass is concentrated by centrifugation and returned to the anaerobic reactor (volume $V_B$). There is a problem in that a lag phase may be observed before aerobic cells become adapted to anaerobic metabolism. Hence it may be advantageous to operate reactor B under oxygen limitation or to interpose an intermediate 'anaerobic adaptation' reactor fed with low sugars at optimum growth pH before the cells return to the catalytic stage.

The process variables in such a reactor configuration are complex, but the system has a redeeming feature. Optimal ethanol yield for any given feed composition and rate ($V_S$) occurs when anaerobic $CO_2$ (=ethanol) production is maximal and aerobic $CO_2$ (assuming complete sugars oxidation) is minimal. Optimal productivity is given by maximizing $V_S$. Hence by using $CO_2$ sensors to control the pump rates, pH and temperature in each vessel, the system lends itself to self-optimisation. This is a considerable advantage in minimizing pilot plant development work with any particular substrate and an even greater advantage at plant scale in dealing with feedstocks of variable composition.

SUMMARY

In its preferred form, now summarised but without derogation from the claims, the present invention uses mutants of an extremely thermophilic facultative anaerobe such as the novel *Bacillus stearothermophilus* strain LLD-R (NCIB 12403) capable of rapid aerobic and anaerobic growth and/or metabolism above 70° C. with a wide range of sugars including pentoses and cellobiose arising from hydrolysis of lignocellulose. The mutants, such as strain *Bacillus thermophilus* LLD-15 (NCIB 12428), are desirably selected so as to switch anaerobic pathways predominantly towards ethanol production. These are the deposited strains referred to herein.

Strain LLD-R grows rapidly on a wide range of sugars up to 75° C. but the major anaerobic product is L-lactate. The mutant strain LLD-15 grows equally rapidly via two major energy pathways : the pyruvate - formate lyase (PFL) pathway yielding 1 mole ethanol, 1 acetate and 2 formate/mole glucose residue, and a previously unrecognised pyruvate dehydrogenase (PDH) pathway yielding 2 ethanol + 2 $CO_2$/mole glucose.

The metabolic flux in strain LLD-15 can be directed through the PDH-pathway by manipulation of physiological conditions, in particular a build-up of pyruvate caused by growth at acid pH or by the presence of acetate and formate in the medium. Higher temperatures also favour the PDH-pathway. The cells may not grow under such conditions but continue to convert sugars to ethanol. Alternatively the PDH-flux can be increased by further mutations; for example mutations which suppress acetate production. Other desirable mutations are those which increase total anaerobic pyruvate dehydrogenase activity, since this is rate-limiting for ethanol productivity.

Such strains are optimal for a two-stage fermentation in which catalytic biomass is first grown in an aerobic seed stage and subsequently used anaerobically in an ethanol production stage without growth. This can be achieved in a single-stage batch or fed-batch reactor, with continuing ethanol removal in the vapour phase to allow use of concentrated sugar feedstocks. Conventional feedstocks such as glucose, sucrose or maltose may be used, but also sugars arising from hydrolysis of lignocellulosic wastes including pentoses and cellobiose.

The strains are not very suitable for conventional single-stage continuous cultures but may be used to advantage in a single stage system with partial cell recycle or in a two-stage continuous system in which sugars are fed to an anaerobic catalytic reactor with continuing ethanol removal in the vapour. The remaining ethanol is stripped from the aqueous effluent from this reactor and the residual carbon sources are utilised to create new catalytic biomass in an aerobic biomass stage. Thereby effectively all of the potential substrates in the feedstocks are utilised either anaerobically or aerobically. Moreover this system lends itself to automated self-optimisation for ethanol production by maximising anaerobically-produced $CO_2$ (equivalent to biomass production). This can be a particular advantage when using mixed and variable feedstocks.

REFERENCES

1. Hartley, B. S. et. al. (1983) In *'Biotech 83'* Online Publications Ltd., Northwood, U. K., p. 895.
2. Hartley, B. S. and Shama, G. (1987) In *'Utilisation of Cellulosic Wastes'* (eds. Hartley, B. S., Broda, P.M.A., and Senior, P.), The Royal Society, London.
3. Payton, M. A. and Hartley, B. S. (1985) *FEMS Microbiol. Lett.* 26, 333.
4. Ragg, P. L. and Fields, P. R. In *'Utilisation of Lignocellulosic Wastes'* (Eds. Hartley, B. S., Broda P.M.A. and Senior, P.), The Royal Society, London.

I claim:

1. A two-stage closed system process for the production of ethanol comprising
   (i) carrying out ethanol-producing anaerobic fermentation of sugars in an anaerobic fermentation medium at a temperature of at least about 70° C. in the presence of a thermophilic, facultatively anaerobic bacterium capable of fermenting sugars both aerobically and anaerobically and producing ethanol in anaerobic fermentation at temperatures 70° C. or above;

(ii) continuously removing ethanol during anaerobic fermentation (i);

(iii) continuously withdrawing a portion of the fermentation medium from anaerobic fermentation (i);

(iv) separating bacteria from the withdrawn fermentation medium and recycling the separated bacteria to anaerobic fermentation (i);

(v) removing ethanol from the withdrawn portion of the fermentation medium;

(vi) adding the ethanol free fermentation medium to an aerobic reactor and culturing the bacteria, returning a portion of the resulting bacteria and the medium to the anaerobic fermentation medium of anaerobic fermentation (i) so as to maintain catalytic biomass.

2. The process according to claim 1, wherein said strain produces maximum yields of ethanol while minimizing anaerobic growth of said strain.

3. The process according to claim 1, wherein anaerobic and aerobic $CO_2$ production is monitored and the anaerobic $CO_2$ to aerobic $CO_2$ ratio is maximized for each of the process conditions employed.

4. The process according to claim 2, wherein the strain lacks NAD-linked lactate dehydrogenase activity.

5. The process according to claim 1, wherein the strain produces ethanol in said anaerobic fermentation by pyruvate dehydrogenase pathway activity.

6. The process according to claim 2, wherein the strain during said anaerobic fermentation suppresses pyruvateformate lyase pathway flux.

7. The process according to claim 1, wherein said sugars comprise pentoses or cellobiose.

8. The process according to claim 1, wherein the thermophilic, faculatively anaerobic bacterium is a strain of *Bacillus stearothermophilus*.

9. The process according to claim 8 wherein the strain is selected from the group consisting of *B. stearothermophilus* LLD-R (NCIB 12403) and *B. stearothermophilus* LLD-15 (NCIB 12428) and ethanol producing variants and derivatives thereof.

* * * * *